United States Patent
Kamath

(10) Patent No.: US 6,972,184 B2
(45) Date of Patent: Dec. 6, 2005

(54) CELL MOTILITY ASSAY

(75) Inventor: Lakshmi Kamath, Chelmsford, MA (US)

(73) Assignee: Millipore Corporation, Billerica, MA (US)

(*) Notice: Subject to any disclaimer, the term of this patent is extended or adjusted under 35 U.S.C. 154(b) by 0 days.

(21) Appl. No.: 10/746,029

(22) Filed: Dec. 23, 2003

(65) Prior Publication Data

US 2005/0136506 A1 Jun. 23, 2005

(51) Int. Cl.[7] .................. C12M 1/00; C12N 1/00; C12N 5/00; C12N 5/02; C12Q 1/02
(52) U.S. Cl. ............... 435/29; 435/243; 435/283.1; 435/325
(58) Field of Search .................. 435/325, 243, 435/29, 283.1

(56) References Cited

U.S. PATENT DOCUMENTS

| | | | |
|---|---|---|---|
| 4,535,414 A * | 8/1985 | Lemelson .................... 364/561 |
| 5,210,021 A | 5/1993 | Goodwin, Jr. ............... 435/29 |
| 5,284,753 A | 2/1994 | Goodwin, Jr. ............... 432/30 |
| 5,302,515 A | 4/1994 | Goodwin, Jr. ............... 435/29 |
| 5,601,997 A | 2/1997 | Tchao ........................... 435/29 |
| 5,959,738 A | 9/1999 | Hafeman et al. ........... 356/440 |
| 6,097,025 A | 8/2000 | Modlin et al. ......... 250/227.22 |
| 6,232,608 B1 | 5/2001 | Giebeler et al. ......... 250/458.1 |
| 6,236,456 B1 | 5/2001 | Giebeler et al. ............. 356/318 |
| 6,274,065 B1 * | 8/2001 | Deno et al. ............. 252/301.16 |
| 6,313,471 B1 | 11/2001 | Giebeler et al. ......... 250/458.1 |
| 6,316,774 B1 | 11/2001 | Giebeler et al. ......... 250/458.1 |
| 6,395,505 B2 | 5/2002 | Goodwin, Jr. ............... 435/29 |
| 6,420,183 B1 | 7/2002 | Krahn et al. ................. 436/164 |
| 6,448,030 B1 | 9/2002 | Rust et al. .................... 435/29 |
| 6,468,786 B2 | 10/2002 | Goodwin, Jr. ........... 435/288.5 |
| 2003/0022269 A1 | 1/2003 | Kirk et al. .................... 435/33 |

FOREIGN PATENT DOCUMENTS

EP 0679195 4/2003 ............ C12Q 1/24

OTHER PUBLICATIONS

"Cell Migration Studies with TECAN Systems", Tecan Corporation Document (dated Sep. 1999) (retrieved from www.tecan.com).
"Analysis of Chemotactic Cell Movement through FATIMA—A Fluorescence Assay for Quantitating Cell Migration In Vitro", Tecan Corporation Document (undated) (retrieved from www.tecan.com).
"FATIMA—Flurescence-Assisted Transmigration Invasion and Motility Assay", Tecan Corporation Document (undated) (retrieved from www.tecan.com).
"OCM Chemotaxis 96-Well Cell Migration Assay", Chemicon Product Literature, Chemicon International, Inc., Revision B: 41266 (Apr. 2002).
L. Karnath et al., "Development of Cancer Cell Invasion Assays in a 96-Well Format", Millipore Corporation Technical Publication (2001) (retrieved from www.millipore.com).
"Multiscreen—MIC Plates"; Millipore Product User Guide, Millipore Corporation, Rev. B, P36448 (Oct. 2002).

* cited by examiner

Primary Examiner—David M. Naff
Assistant Examiner—Deborah K. Ware
(74) Attorney, Agent, or Firm—Nields & Lemack

(57) ABSTRACT

An electrooptical method is disclosed for quantifying the motility response of cells to external stimuli, wherein a target cell population (formed as a function of said response) is subsequently optically differentiated by the addition of an optical differentiation solution, and whereby the targeted cell population becomes more or less detectable to an electrooptical reading device. The method can be used to perform chemotactic assays. For such and other purposes, the method can be performed utilizing high throughput robotic automation.

12 Claims, 3 Drawing Sheets

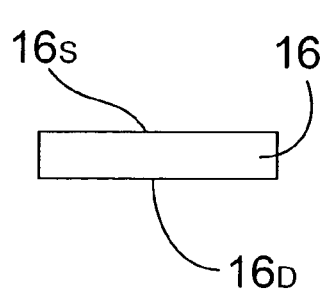
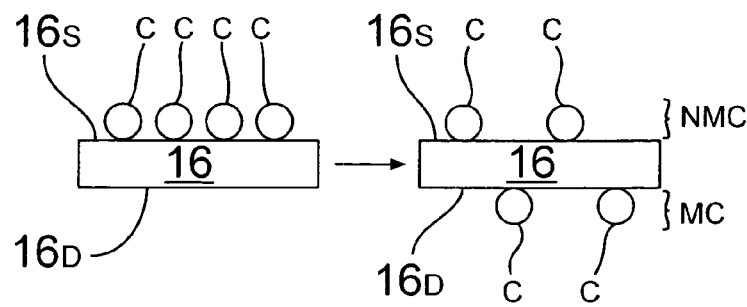
Figure 1a            Figure 1b
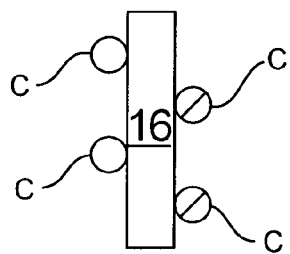
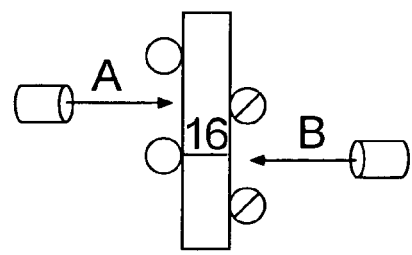
Figure 1c            Figure 1d
Figure 1

CELL MOTILITY ASSAY

FIELD

In general, the present invention is directed to a cell motility assay, and in particular, a cell migration assay useful for studying cellular chemotaxis.

BACKGROUND

Cell movement, either as a chemotactic or chemokinetic response to soluble factors or as a phenomenon governed by a haptotactic response to cell surface or extracellular matrix-associated components, is one of the primary cellular processes during embryonic development, the maintenance of a healthy adult organism, and the progression of a number of pathological conditions, including cancer.

Cell-based assays are widely implemented to study cell motility, and are particularly useful for pre-screening compounds to identify those compounds that can impair cell function and cell behavior. Cancer drug discovery efforts, for example, often incorporate chemotaxis-based cell motility assays to pre-screen and/or discover potential and promising drug candidates.

Conventional chemotaxis assay procedures are well known. For example, according to one procedure, adherent cells are deposited onto one surface of an isoporous translucent polycarbonate membrane and placed within a solution containing a concentration gradient of pre-selected chemoattractant. Often, but not always, the chemoattractant is the subject of the investigation. The cells gradually move through the pores of membrane, from one surface to another, towards or away from higher or lower concentrations of the chemoattractant. The cells form migrant and non-migrant cell populations on respective sides of the membrane. The cells are then manually scraped off one surface of the membrane, and the remaining cells on the other surface are labeled with a fluorescent compound and "counted" with a scanning fluorometer.

While this and like procedures are adequate for low throughput single-sample chemotactic assays (for example, for small-scale academic research), when seeking much higher throughput (for example, for large-scale industrial drug discovery efforts), the need to conduct several contemporaneous assays (for example, utilizing multi-segmented receptacles having several discrete assay chambers) becomes particularly acute. However, the difficulty of the physical steps involved in a single-sample assay are compounded when several instances of those steps are performed contemporaneously in (typically) smaller sample sizes.

In particular, the step of removing non-migrant cells in a single chemotactic assay can be performed with comparative ease and efficacy. However, the same step conducted for ninety-six chemotactic samples, for example, plated within a 96-well multi-well array is difficult and prone to human error. More time, more effort, more care, and a higher level of technical skill is needed to manually scrape off cells. Often, each chamber must be individually and manually scrubbed, with each instance susceptible to cross contamination between the chambers and/or inadvertent membrane rupture.

An alternative is suggested recently by U.S. Pat. No. 5,601,997, issued to R. Tchao on Feb. 11, 1997.

The Tchao patent discloses a chemotactic methodology that utilizes a custom-engineered multi-well array as its assay sample platform. This multi-well array —unlike many comparable currently-available arrays—incorporates a "radiation opaque membrane". The radiation opaque membrane is disclosed as "having a plurality of substantially perpendicular pores" and is "not substantially transmissive" of "at least one" of certain defined wavelengths of electromagnetic radiation used in the course of assay. When an optical scanner is used for a fluorescence reading of labeled cells, the radiation opaque membrane blocks the passage of light, thus discouraging—as intended—both fluorescent activation and detection by the scanner of cells on the far opposite surface of the membrane.

The Tchao patent provides an approach for conducting chemotactic assays that does not require manual cell removal prior to fluorescent scanning. Regardless, need remains for alternative approaches, particularly one that does not require the use of a custom-designed "radiation opaque membrane".

SUMMARY

Responsive to the above need, and other long felt needs, the present invention provides, in general, an electrooptical method for quantifying the motility response of cells to external stimuli, wherein a target cell population (formed as a function of said response) is subsequently optically differentiated by the addition of an optical differentiation solution, and whereby the targeted cell population becomes more or less detectable to an electrooptical reading device.

The method can be conducted utilizing a comparatively broad variety of assay platforms (e.g., 96-well multi-well arrays), including "generic" transwell platforms. The method can also be conducted from commencement through completion, with neither any substantial physical disassembly of a utilized assay platform, nor any substantial intervening direct manual cell removal. The method is, for these and other factors, well-suited for high-throughput robotic automation.

The method comprises particularly the steps of depositing cells (e.g., adherent tumor-causing cells) on a porous film (e.g., track-etched isoporous polycarbonate membrane); promoting migration of a portion of said cells from through said porous film (e.g., by establishing and placing the cells within a concentration gradient of a pre-selected chemoattractant); adding an optical differentiation solution to either the migrant or non-migrant cell portion to render said treated portion more or less detectable by an electrooptical reading device (e.g., a scanning fluorometer); then "counting" (directly or indirectly) either the migrant and/or non-migrant cell population utilizing said electrooptical reading device.

In light of the above, it is a principal object of the present invention to provide an electrooptical method for quantifying the motility response of cells to external stimuli, wherein a target cell population (formed as a function of said response) is subsequently optically differentiated by the addition of an optical differentiation solution.

It is another object of the present invention to provide a method for conducting a chemotactic assay that can be conducted utilizing a conventional electrooptical reading device and a generic chemotactic transwell assay platform (e.g., one without custom-made light blocking membranes).

It is another object of the present invention to provide a method for conducting a chemotactic assay that can be conducted utilizing a conventional electrooptical reading device and a chemotactic transwell assay platform, and that is well-suited for robotic automation.

It is another object of the present invention to provide a kit of pre-selected compatible components suitable for conducting pre-selected modes of practicing the inventive method.

It is another object of the present invention to provide an optical attenuation solution useful for a comparatively broad range of modes of conducting the inventive method.

These and other objects can be further appreciated in light of the detailed description herein of the invention according to certain of its current embodiments, considered together with the attached drawings.

BRIEF DESCRIPTION OF THE DRAWINGS

FIGS. 1a to 1d illustrate schematically a method for promoting, differentiating, and quantifying the chemotactic migration of cells C across a porous film 16, from one surface $16_S$ to another $16_D$.

DETAILED DESCRIPTION

Figure 2A:
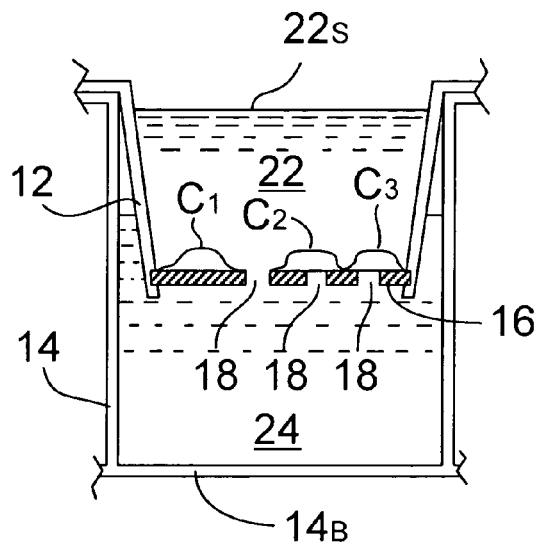
FIGS. 2a to 2d illustrate schematically in comparatively greater detail the method illustrated in FIGS. 1a to 1d.
Figure 2B:
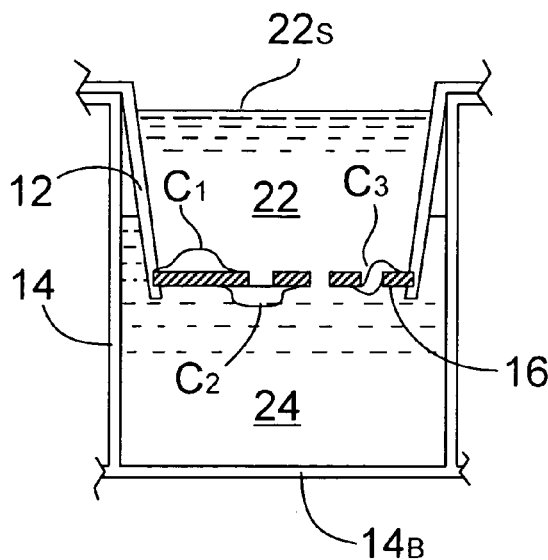
Figure 2C:
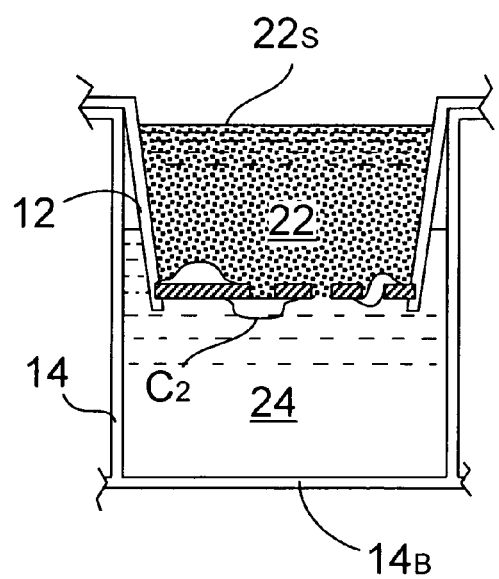
Figure 2D:
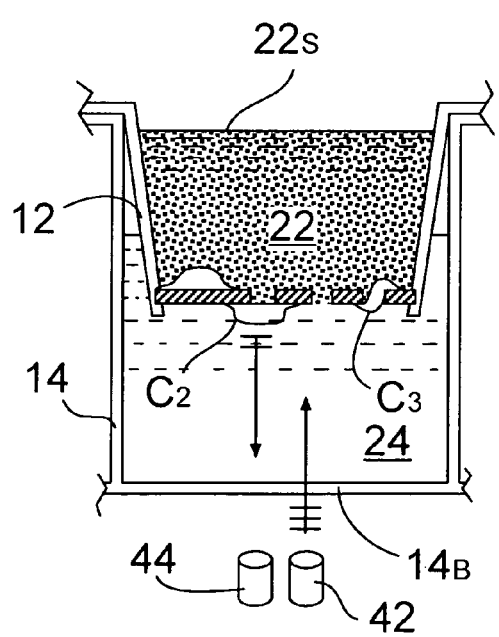

The present invention enables quantification of otherwise indistinguishable migrant and non-migrant cell populations by optically differentiating said cell populations, then utilizing an electrooptical reading device to detect the resultant differentiating optical property. The basic steps that comprise the method are illustrated schematically in FIGS. 1a, 1b, 1c, and 1d.

The method commences, as shown in FIG. 1a, with the provision of a porous film 16 having a "starting surface" $16_S$ and a "destination surface" $16_D$.

A population of cells C are, as shown in FIG. 1b, deposited on the starting surface $16_S$ of the porous film and conditions established to promote migration of a portion of said cells from said starting surface $16_S$ to said destination surface $16_D$ through said porous film 16. At the conclusion of this step, the original population of cells C are divided by porous film 16 into yet "optically-indistinguishable" migrant and non-migrant cell populations MC and NMC.

The method continues, as represented in FIG. 1c, by adding an "optical differentiation solution" to either the portion of the cells remaining on the starting surface (i.e., the aforementioned non-migrant cell population NMC) or the portion of the cells migrating to the destination surface (i.e., the aforementioned migrant cell population MC) to render the treated portion more or less detectable by a pre-selected electrooptical reading device. At the conclusion of this step, the migrant and non-migrant cell populations MC and NMC are "optically-differentiated".

The method concludes, as shown in FIG. 1d, with the utilization of the aforementioned pre-selected electrooptical reading device to read the optically-differentiating property of: Either the cells C that remain on the starting surface $16_S$ or the cells C that migrated to the destination surface $16_D$ (cf., optical scans "A" or "B"); or both migrant and non-migrant cell populations (cf., optical scans "A" and "B").

The step of adding an optical differentiation solution—key to the practice of the present invention—is subject to variation. Regardless, four general modes of practice can be identified.

In a first general mode of practice, the optical differentiation solution is designed to "diminish" the optical signal attributable to the non-migrant cells NMC. A process utilizing such solution commences, for example, by initially and non-selectively labeling all cells prior to effecting cell migration with a fluorescing compound, then selectively deactivating, masking, quenching, or otherwise diminishing said fluorescence by adding said optical differentiation solution (appropriately configured) to the non-migrant cells NMC.

In a second general mode of practice, the optical differentiation solution is designed to "diminish" the optical signal attributable to the migrant cells MC. A process utilizing such solution commences, for example, by initially and non-selectively labeling all cells prior to effecting cell migration with a fluorescing compound, then selectively deactivating, masking, quenching, or otherwise diminishing said fluorescence by adding said optical differentiation solution (appropriately configured) to the migrant cells MC.

In a third general mode of practice, the optical differentiation solution is designed to "enhance" the optical detectability of the non-migrant cells NMC. A process utilizing such solution commences, for example, by promoting the migration of cells from an optically undifferentiated cell population, then selectively enhancing the non-migrant cells NMC by selectively treating them with said optical differentiation solution. An optical differentiation solution configured for such functionality can include, for example, a fluorescent compound as one of its components.

Finally, in a fourth general mode of practice, the optical differentiation solution is designed to "enhance" the optical detectability of the migrant cells MC. A process utilizing such solution commence, for example, by promoting the migration of cells from an optically undifferentiated cell population, then selectively enhancing the migrant cells MC by selectively treating them with said optical differentiation solution.

The step of promoting the migration cells from a film's starting surface to its destination surface can involve one of the many standard and well-known chemotactic protocols, but can involve other protocols involving other chemokinetic mechanisms.

Chemotaxis in general involves the directed movement of a motile cell or organism in response to a specific chemical concentration gradient. In the present invention, this can occur either towards a higher concentration (i.e., positive chemotaxis) or towards a lower concentration (i.e., negative chemotaxis).

The cells typically under investigation in a chemotaxis-based assay are, so-called "adherent" cells (i.e., cells that survive and proliferate as monolayer culture when attached to a suitable substrate), which includes, but is not limited to, leukocytes (e.g., monocytes and lymphocytes), tumor cells, and prokaryotic and eukaryotic microorganisms. The tumor cells can be derived, for example, from biopsies of breast, lung, and colorectal tissue, as well as hematopoietic cells; and can be of epithelial origin (e.g., carcinomoas), or arise in the connective tissues (e.g., sarcomas), or arise from specialized cells such as melanocytes (e.g., melanomas) and lymphoid cells (e.g., lymphocytes).

In a typical chemotaxis-based assay, a predetermined "chemoattractant" is used in forming a concentration gradient within a solution that is essentially "divided" by the aforementioned porous film. The adherent cells deposited on that porous film migrate from one surface to the other depending on the strength of their attraction or aversion to said chemoattractant. Ultimately, the gradient—which initially is comparatively steep—reaches (by the diffusion of the chemoattractant over time) a state of equilibrium (i.e., a point wherein equal concentrations of chemoattractant exists on both sides of the porous film), and at which point stimulated cell migration ceases. More typically, however, cell migration will be terminated prior to equilibrium at a time dependent upon and defined by the particular protocol being followed.

Once migration is complete, the mechanisms that can enable or promote specificity of differentiation toward either the migrant cells MC or the non-migrant cells are several and diverse. For example, the viscosity of the optical differentiation solution can be tailored to frustrate its flow, as well as any solid constituents suspended or otherwise borne thereon, through the porous film for at least the duration appropriate to optically read the optically differentiating property of the targeted cells. Alternatively, the optically-functional constituent of the optical differentiation solution can be selected from or configured as physically large solid or particulate material having dimensions suitable to prevent or otherwise restrict its passage through the pores of the porous film.

Specificity can also be enabled by chemical mechanisms. For example, the solutions on opposing sides of the porous film during the optical differentiation step (i.e., subsequent to the conclusion of cell migration) are changed or modified to render the solutions substantially immiscible, such as by replacing substantially all of an aqueous (typically hydrophilic) chemoattractant solution, on one side of the porous film only, with an organic hydrophobic optical attenuation solution. Alternatively, a selective non-optical pretreatment (e.g., the addition of binding sites) can be employed, targeting specifically either the migrant cells MC or the non-migrant cells NMC, that renders one and not the other reactive or otherwise responsive to the optically-functional component of the optical differentiation solution.

As will be appreciated, the "selectivity" of the optical differentiation step can involve the addition of a single optical differentiation solution immediately after the cell migration or can involve additional sequences, such as the aspiration of spent chemoattractant solution, and the washing and pre-treatment of the cells. The former is preferred inasmuch as its single-stage differentiation step is well suited for robotic automation. The latter is preferred inasmuch as its multi-stage differentiation step provides greater flexibility in the configuration and implementation of the optical differentiation solution.

The operative conditions for the conduct of the present invention for a chemotactic investigations are as follows: The temperature should approximate human body temperature (i.e., 37° C.); the solutions used are all aqueous with constituency, concentrations, and pH tailored to favor cell viability and motility; the cells investigated are adherent cells; and the pressure is normal ambient pressure. The typical duration allocated for cell migration in current chemotactic protocols under such circumstances (commencing from the establishment of a chemoattractant concentration gradient) is approximately four to six hours.

The configuration of the optical differentiation solution will differ depending on the application of and particular mode of performing the inventive methodology. The optical differentiation solution can function on the basis of, for example, selective optical attenuation (e.g., masking, quenching, and absorption), selective optical enhancement (e.g., fluorescent labeling, and staining with a dye, colorant, or luminescent compound), or selective lysing (i.e., the partial or complete obliteration or removal of either the migrant or non-migrant cell population in combination with non-selective optical enhancement). Selective optical attenuation can be effected directly upon targeted cells (e.g., by quenching chelated membrane-bound fluorescent compounds); or effected indirectly by modifying the optical properties of the media solution hosting, harboring, or proximate said cell population (e.g., by adding light absorbing material into said media solution to mask or absorb light propagated from, within, or toward the targeted cell population).

The optical differentiation solution can be an aqueous or organic solution, or an emulsion, suspension, or dispersion, and will typically comprise therein at least one primary optically-functional compound, phase, particle, or other like component. The primary optical functional component is selected to enable optical differentiation. While it may also be responsible for the invention's selectivity, selectivity can also be made a function of the remainder of the solution upon which that component is borne.

In a preferred optical differentiation solution, the primary optically-functional component is a particle capable of broad spectrum (preferably, so-called "black body") light absorption, for example, carbon black. Carbon black and carbon black compositions can be obtained commercially, in varying grades and particle sizes, from such manufacturers as Cabot Corporation (Billerica, Mass.), Degussa Huls AG (Frankfurt, Germany), E.I. du Pont de Nemours, Inc. (Wilmington, Del.), and Columbian Chemicals Company (Marietta, Ga.).

If the particles size of the carbon black is smaller than the nominal pore size of the porous film, then the optical differentiation solution should preferably have a comparatively high viscosity, i.e., a viscosity sufficient to minimize or render negligible the flow thereof through the porous film for the duration of the optical reading. Alternatively, larger particles comprising agglomerates of carbon black can be used to allow greater latitude in designing the solution's viscosity. Such larger particle may not provide a high degree of "masking" functionality, but can nonetheless absorb scattered light, and thus contribute to the attenuation of an unwanted optical background signal.

Although the primary optical functional component of an optical attenuation solution need only absorb light within the light sensitivity range of the selected electrooptical reader, it will be appreciated that commercially available readers will not only differ among themselves in respect of their optical sensitivities, but many readers themselves are capable of being tuned to a number of different optical ranges. The use of carbon black is thus preferred over other more narrowly absorptive components—particularly in the "kit" embodiments of the present invention—because its broad absorptivity enables use for a number of different assays utilizing different electrooptical readers.

A particular embodiment of an optical attenuation solution, suitable for use in a calcein-labelled chemotactic assay, is an aqueous solution of carbon black in glycerol, wherein the concentration of carbon black is at least approximately 0.05% (wt/vol.) and the concentration of glycerol is within the range of approximately 5% to approximately 75% (wt/vol.). For most chemotactic and chemokinetic analyses, such aqueous optical attenuation solution will consist only of the carbon black and the glycerol components, attenuation being controlled by the carbon black component, and selectivity being controlled by the glycerol component. The addition of other ingredients (such as surfactants, bactericides, preservatives, and the like), while not categorically foreclosed, should be considered in light of the particular impact, if any, of such ingredients on, for example, cell viability, cell motility, and fluorescence.

The assay of the present invention is conducted on a platform that at the least comprises a porous film placed in a position intermediate a first and second zone (e.g., the upper and lower zones of a receptacle "divided" by said porous film). Although structurally divided by the porous film, the first and second zones are at a microscopic level "continuous", i.e., through the pores of the porous film. Such continuity enables, for example, the creation of a concentration gradient of chemoattractant between the first and second zones, as well as the migration of cells from one surface of the porous film (i.e., the "starting" surface) to the other (i.e., the "destination" surface) in response to said concentration gradient. Cells essentially "crawl" through the pores of the film.

Although practice of the inventive methodology is not limited in respect of the selection of a porous film, advantages are realized by selecting a film having a pore structure that facilitates cell migration. A particularly useful species of porous film are so-called "isoporous" membranes. In contrast with membranes that have a tortuous pore network—currently the more commercially-common membrane configuration—the pores of an "isoporous" membrane are discrete channels (cf., capillaries) that traverse the membrane from one surface to another with little if any lateral or cross-channel deviation.

Particularly suitable isoporous membranes are those that have a smooth, glass-like surface that enables clear sample observation, and is non-reactive to any stains, dyes, or fluorescent or luminescent compounds used in the course of the assay.

Suitable isoporous membranes can be obtained through many available commercial venues. For example, isoporous polycarbonate membranes in 0.05, 0.1, 0.22, 0.4, 0.6, 0.8, 1.2, 2, 3, 5, 8, 10, and 12 micron pore diameters are available from Millipore Corporation of Billerica, Mass., under the tradename "Isopore". Other commercial sources of isoporous membranes include, but are not limited to, the Whatman Corporation of the United Kingdom (e.g., "Nuclepore" and "Cyclopore" lines of polycarbonate track-etched membrane); and the Becton-Dickinson Company of Franklin Lakes, N.J. (e.g., "BD Falcon" line of polyethylene terephtalate-based track-etched membrane).

Although the advantages of the present invention are more fully apparent when utilizing light transmissive or translucent porous films, so-called "black" membranes (e.g., "Fluoroblok" membrane available from the Becton-Dickinson Company) can also be utilized. (See also, U.S. Pat. No. 5,601,997, issued to R. Tchao on Feb. 3, 1995.) Although such membranes are already designed to block undesired background signal noise, light leakage may still occur through a black membrane's pores. Use of the methodologies herein can, for example, improve optical scan data by removing or lessening the detectability or occurence of such light leakage.

Isoporous membranes can be formed, for example, by known "track-etch" methodologies. Such methodologies in general involve bombarding a solid film with particles or energy that form tracks of damaged material through the film. The film is then subjected to a chemical agent that selectively etches the damaged tracks to create perforations through the film. The diameters of the perforations can be controlled by the residence time of the etchant on the film. Thus, the film can be provided with pores that all are equal to or smaller than a desired maximum pore size. Examples of processes for forming track-etched membranes are disclosed in U.S. Pat. No. 3,303,085, issued to P. B. Price et al. on Feb. 7, 1967; U.S. Pat. No. 3,662,178, issued to R. W. Caputi et al. on May 9, 1972; U.S. Pat. No. 3,713,921, issued to R. L. Fleischer et al. on Jan. 30, 1973; U.S. Pat. No. 3,802,972, issued to R. L. Fleischer et al. on Apr. 9, 1974; and U.S. Pat. No. 3,852,134, issued to C. P. Bean on Dec. 3, 1974.

Figure 3:
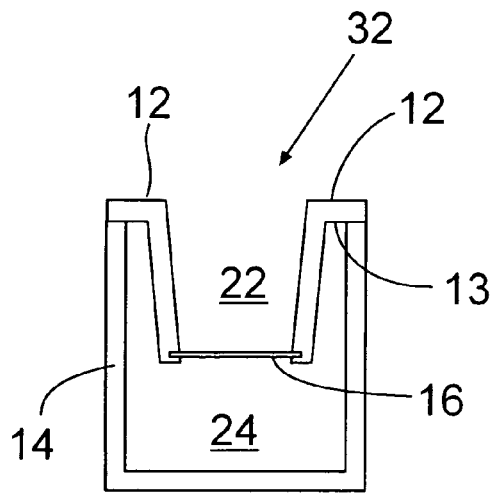
FIG. 3 illustrates schematically a pair of nested fluid receptacles 12 and 14 useful for conducting the method illustrated by FIGS. 1a to 1d, the receptacles being constructed according to one embodiment thereof.
Figure 4:
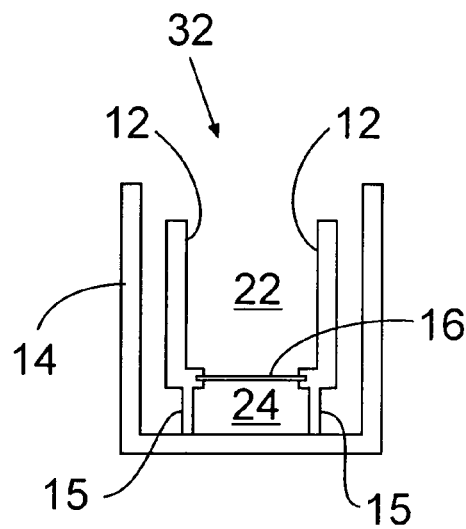
FIG. 4 illustrates schematically a pair of nested fluid receptacles 12 and 14 useful for conducting the method illustrated by FIGS. 1a to 1d, the receptacles being constructed according to another embodiment thereof.

A typical platform which incorporates said porous film and is suitable for conducting the inventive methodology comprises, as shown in FIGS. 3 and 4, a pair 32 of nested fluid receptacles 12 and 14. The top and bottom fluid receptacles 12 and 14 are configured such that when appropriately combined or otherwise paired (i.e., "nested") an upper zone 22 and lower zone 24 is formed with the porous film 16 therebetween. In performing the inventive methodology, the "starting" surface of the porous film 16 will typically (but not always) face the upper zone 24, with the "destination" surface facing the lower zone 24.

The practice of the present invention is not restricted in respect of any particular structural configuration of nested fluid receptacles 32, the sizes, dimensions, construction, and shapes thereof being subject to substantial variation. However, in all embodiments thereof the receptacles will be configured to enable the propagation of light from the selected electrooptical reading device to at least one surface of the porous film. Hence, for example, if the selected electrooptical reading device is of a "bottom-reading" variety, then the bottom wall (i.e., the floor) of the bottom fluid receptacle 14 should be appropriately and substantially light transmissive.

If desired, the walls of either or both the top and bottom fluid receptacles 12 and 14 can be configured to provide additional optical functionality, for example, the provision of coated or otherwise light absorptive side walls that minimize lateral light reflection and scattering, or the configuration of the bottom wall of the bottom fluid receptacle as an integrated optical element (e.g., a concave or convex lens, a collimator, a diffuser, a polarizer, a filter, or a diffractor).

As illustrated in FIGS. 3 and 4, the manner in which top and bottom fluid receptacles 12 and 14 are "nested" is also subject to variation. For example, in FIG. 3, the top fluid receptacle 12 is nested within bottom fluid receptacle 14 utilizing an annular flange or lip or brim 13 that extends past the diameter of the lower fluid receptacle 14, and thereby suspends the top fluid receptacle 12 within the bottom fluid receptacle 14, essentially hanging over the floor thereof. In contrast, in FIG. 4, the top fluid receptacle 12 is provided with a plurality of stilts or legs 15 that enable said receptacle 12 to be seated directly on the floor of the lower fluid receptacle 14.

Although the porous film 16 is shown in FIGS. 3 and 4 incorporated as an integral component of the top fluid receptacle 12, such integration is not in all instances a fundamental requirement of the present invention. In certain applications, the inventive methodology can be practice utilizing nested fluid receptacles wherein the porous film is either incorporated into either the top fluid receptacle, or the bottom fluid receptacle, or neither. Regarding the latter, a porous film can initially be provided as a stand-alone or otherwise separate component that becomes interposed between the upper and lower zones of the top and bottom fluid receptacles only, for example, during manufacture of a nested fluid receptacle platform, or during or immediately prior to the conduct of the inventive methodology by the practitioner thereof.

Although the present invention can be practiced using a single pair of nested fluid receptacles, a principal advantage of the present invention is its amenability to automated robotic handling. Hence, in a preferred mode of practice, a multi-well array is utilized.

Figure 5:
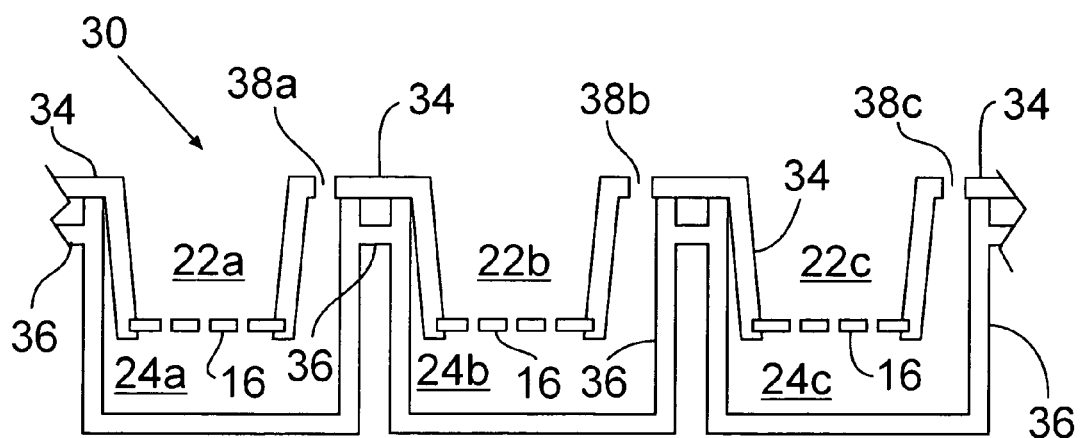
FIG. 5 illustrates schematically a multi-well array 30 useful for conducting the method illustrated by FIGS. 1a to 1d, the multi-well array being constructed according to one embodiment thereof.

A representative example of a multi-well array 30 is illustrated in FIG. 5. As shown therein, the multi-well array 30 comprises several nested pairs of fluid receptacles. More particularly, the multi-well array comprises an upper plate 34 and a lower plate 36, wherein: the upper plate comprises a plurality of top fluid receptacles 22a, 22b, and 22c; the lower plate comprises a corresponding plurality of bottom fluid receptacle 24a, 24b, and 24c; and porous film 16 is disposed between the top and bottom receptacles. In an alternative embodiment (not shown), a plurality of individual (i.e., separate) top fluid receptacles (such as illustrated in FIGS. 3 and 4) are nested within an array of bottom fluid receptacles fixedly disposed in a lower plate.

To provide access to fluid contained in the bottom fluid receptacles 24a, 24b, and 24c—for example, after the commencement of an assay with both plates 34 and 36 engaged—a corresponding plurality of openings 38a, 38b, and 38c are provided through the upper plate in area outside the top fluid receptacles 22a, 22b, and 22c, yet within the ambit of the each respective bottom fluid receptacle 24a, 24b, and 24c. A multi-well array 30 having such openings is particularly preferred when, for example, an optical enhancement solution is added, in accordance with the present invention, to the bottom fluid receptacles to selectively enhance the detectability of a migrant cell population by a bottom-reading electrooptical reader. Without such fluid-access openings, disassembly of the plates 34 and 36 may be needed to enable such step, and while possible, it is time-consuming and potentially disruptive.

Further details regarding the manufacture, structure, and useful alternative embodiments of multi-well arrays can be found in or extrapolated from widely available published technical literature, such as, for example, the following patent documents: U.S. Pat. No. 5,302,515, issued to R. H. Goodwin, Jr. on Apr. 12, 1994; U.S. Pat. No. 5,650,323, issued to D. Root et al. on Jul. 22, 1991; U.S. Pat. No. 5,047,215, issued to R. Manns on Sep. 10, 1991; U.S. Pat. No. 5,035,866, issued to J. C. Wannland on Jul. 30, 1991; U.S. Pat. No. 5,026,649, issued to G. Lyman et al. on Jun. 25, 1991; and U.S. Pat. No. 5,009,780, issued to M. J. Sarrasin on Apr. 13, 1991.

The number of nested fluid receptacles (i.e., "wells") in commercially available multi-well arrays that are designed specifically for cytological transwell assays are most commonly 6, 24, 96, and 384. In the practice of the present invention, 24- and 96-well arrays are currently preferred.

Electrooptical reading devices capable of detecting in a cell population the optical properties of interest can vary substantially. Regardless, in accordance with the present invention, all such devices will comprise at the least a phototransmitter 42 and a photoreceptor 44. The phototransmitter 52 propagates light within a predetermined wavelength range towards a targeted cell population directly or along a non-linear optical pathway. Upon impingement upon the cells, depending on the selected mode of practice, the light is either reflected off the cells, or it causes or otherwise leads to fluorescence, luminescence, or other optically-detectable photoconversion. Whichever case, the light propagating away from the cells impinges upon the photoreceptor 44, which is positioned appropriately for such purpose, and is provided with the means to convert said light into electronic data.

An electrooptical reading device will also comprise additional optical components that define the optical pathways traversed by light as it propagates between the targeted cells, the phototransmitter 52, and photoreceptor 44. Such additional optical components can include lenses, collimators, diffractors, polarizers, retarders, filters, prisms, and reflectors. The placement of these and like optical components will determine whether the electrooptical reading device is, for example, "bottom-reading", "top-reading", or both.

The electrooptical reading device can also further comprise an automated sample tray capable of receiving and holding the pre-selected assay platform (e.g., a 96 well multi-well array), and moving said assay platform into and out of operative position within the guts of the electrooptical reading device prior to and after conduct of an optical scan.

An electronic control system (or subcomponents thereof) can be incorporated into and/or linked peripherally with the electrooptical reading device. Certain functions of such electronic control system include controlling and coordinating the operation of other components of the electrooptical reading device (e.g., the photoreceptor, phototransmitter, and sample tray); and recording, obtaining, and/or processing electronic data (e.g., the electronic data generated by the photoreceptor 44. The electronic control system can comprise, for example, a CPU, an information display, an input device, an output device, electronic memory, cables, installed software, data storage devices, printed circuit boards, printed wiring boards, peripheral interface cards, and the like.

The preferred electrooptical reader is an automated multi-well plate capable spectrofluorometer. Commercially-available variants of such multi-well plate readers include, but are not limited to: "Fluoromark"-brand reader, available from Bio-Rad Laboratories of Hercules, Calif. 94547 (a top and bottom reading device having a wavelength range of 250 to 290 nm); "NOVOstar"-brand reader, available from BMG Labtechnologies GmbH of Offenburg, Germany (a bottom reading device having a wavelength range of 250 to 740 nm); "Fluoroscan Ascent"-brand reader, available from Thermo Electron Corpoaration of Waltham, Mass. 02451 (a top and bottom reading device having a wavelength range of 320 to 800 nm); "Hitachi FMBIO II Florescence"-brand reader, available from MiraBio, Inc., of Alameda, Calif. 94502 (a bottom reading device having a wavelength range from 50 to 700 nm); "FLIPR"-branded readers, available from Molecular Devices Corporation of Sunnyvale, Calif. 94089 (a bottom reading device having a wavelength range from 488 to 514 nm); "FluorImager"-brand reader, available from Amersham Biosciences, Piscataway, N.J. 08854 (a bottom reading device having a wavelength range from 430 to 635 nm); "Fluorocount"-brand reader, available from PerkinElmer, Inc., Wellesley, Mass. 02481 (a top and bottom reading device having a wavelength range from 260–670 nm); "Cytofluor"-branded reader, available from Applied Biosystems, Foster City, Calif. 94404 (a top and bottom reading device having a wavelength range from 320 to 700 nm); and "Polarion"-brand reader, available from Tecan Group, Ltd., of Maennedorf, Switzerland (a top reading device having a wavelength range from 230 to 700 nm).

As an alternative to fluorescence- and luminescence-based electrooptical reading devices, one may also, for example, utilize or assemble a device capable of automated microscopic enumeration of cells within a targeted population. In this regard, light reflected from the optically-differentiated cells of a specifically targeted cell population provides an image of said cells that is "machine-viewed" through a suitably equipped microscope. Image processing software installed within or for such reader then "counts" the cells using known image analysis algorithms. In a specific embodiment of such system, optically differentiated cells are imaged, for example, using a Fuji Finepix s1 Pro digital camera mounted on an Olympus BH-2 microscope and counted using Optimas version 6.1 software.

To facilitate use of the inventive methodology for certain cytological applications, in part by standardizing certain of its components, the present invention provides a kit that includes pre-selected compatible components suited for the accomplishment of said applications. Although the kit by design targets pre-selected modes of practicing the inventive methodology, the inclusion of pre-selected compatible components promotes ease of use, consistency of results, and comparatively lower user costs.

In one embodiment, the chemotactic assay kit is designed specifically for the conduct of certain prescribed fluorescence-based chemotactic applications wherein a bottom-reading electrooptical reader is utilized to quantify contemporaneously several migrant cell populations. Such kit will comprise enclosed within a common package: a multi-well array comprising nested or nestable pairs of fluid receptacles, each pair when nested having and upstream zone and a downstream zone separated by a translucent isoporous membrane; and an aqueous optical attenuation solution comprising carbon black and glycerol.

The prescribed chemotactic assay applications of the kit can be provided on labels and/or instructions placed on or accompanying the said kit's "common package". Other additional information that can be provided on or with said labels or instructions include a listing of prescribed bottom-reading electrooptical readers and certain prescribed device (and/or environmental) settings and/or parameters therefor.

The optical attenuation solution is, among other things, configured specifically with the properties of the kit's isoporous membrane, particularly the thickness, average pore, diameter and pore frequency thereof. The optical attenuation solution is thus configured to be substantially incapable of flowing through the isoporous membrane for at least the duration needed to electrooptically "scan" the multi-well array subsequent to the its addition thereinto. For such functionality, the concentration of carbon black in the optical attenuation solution will be at least approximately 0.05% (wt/vol.), with the concentration of glycerol being within the range of approximately 5% to approximately 75% (wt/vol).

In another embodiment, the chemotactic assay kit can further comprise, for example, a cell-labeling solution containing a compound that emits radiation of a predetermined fluorescent bandwidth upon exposure to radiation of a different predetermined exposure bandwidth, for example, calcein, a calcein precursor, or a calcein derivative. Other components can be included in the chemotactic assay kit. However, as with the multi-well array and the optical attenuation solution, the cell-labeling solution and other components should be tailored with a reasonable degree of compatibility with all other included components for at least the performance of at least one of said prescribed chemotactic assay applications.

While the invention has been described with reference to particular embodiments, it will be understood that it is not limited to any of the particular constructions and modes herein disclosed and/or shown in the drawings, but also comprises any modifications or equivalents within the scope of the following claims.

What is claimed is:

1. A method for analyzing cells utilizing an electrooptical reading device capable of detecting an optical property of said cells, the method comprising in order the steps of:
   (a) providing a porous film having a starting surface and a destination surface;
   (b) depositing said cells on the starting surface of said porous film and promoting migration of a portion of said cells from said starting surface to said destination surface through said porous film;
   (c) adding an optical differentiation solution to either the portion of the cells remaining on the starting surface or the portion of the cells migrating to the destination surface to render the portion to which said optical differentiation solution was added more or less detectable by said electrooptical reading device; and
   (d) reading said optical property of said cells remaining on the starting surface or migrating to the destination surface or both utilizing said electrooptical reading device.

2. The method of claim 1, wherein the cells placed in step (b) on the starting surface of said porous film are labeled with a compound that emits radiation of a predetermined fluorescent bandwidth upon exposure to radiation of a different predetermined exposure bandwidth.

3. The method of claim 2, wherein said compound is calcein, a calcein precursor, or a calcein derivative.

4. The method of claim 2 wherein the portion of the cells remaining on the starting surface are rendered less detectable by applying onto the cells that do not migrate to said destination surface and said starting surface said optical differentiation solution, said optical differentiation solution containing a colorant capable of absorbing light at least within said predetermined fluorescent bandwidth, said optical differentiation solution substantially incapable of flowing through said porous film at least for the duration of steps (c) and (d).

5. The method of claim 4, wherein said optical differentiation solution comprises a suspension of said colorant in glycerol, and wherein said colorant is carbon black.

6. The method of claim 5, wherein the electrooptical reading device in step (d) is utilized to detect irradiation within said predetermined fluorescent bandwidth upon exposure of said migrant portion of said cells with irradiation of said predetermined exposure bandwidth, said exposure not passing through said porous film prior to incidence upon said migrant portion of cells.

7. The method of claim 1, wherein the porous film is an isoporous polycarbonate membrane.

8. The method of claim 1, wherein said porous film is provided between nested top and bottom fluid receptacles, said nested fluid receptacle being divided into an upper zone and a lower zone by said porous film.

9. The method of claim 8, wherein said method is conducted utilizing a multi-well array, said multi-well array containing an array of said nested fluid receptacles.

10. The method of claim 9, wherein said multi-well array comprises twenty-four of said nested fluid receptacles.

11. The method of claim 8, wherein the migration in step (b) of said portion of said cells from said starting surface to said destination surface through said porous film is promoted by placing a chemoattractant-containing solution in said lower zone.

12. The method of claim 11, wherein the portion of the cells remaining on the starting surface are rendered less detectable by said electrooptical reading device by adding said optical differentiation solution into said upper zone, said optical differentiation solution containing a colorant capable of absorbing light at least within said predetermined fluorescent bandwidth, said solution substantially incapable of flowing through said porous film at least for the duration of steps (c) through (d).

* * * * *